United States Patent [19]

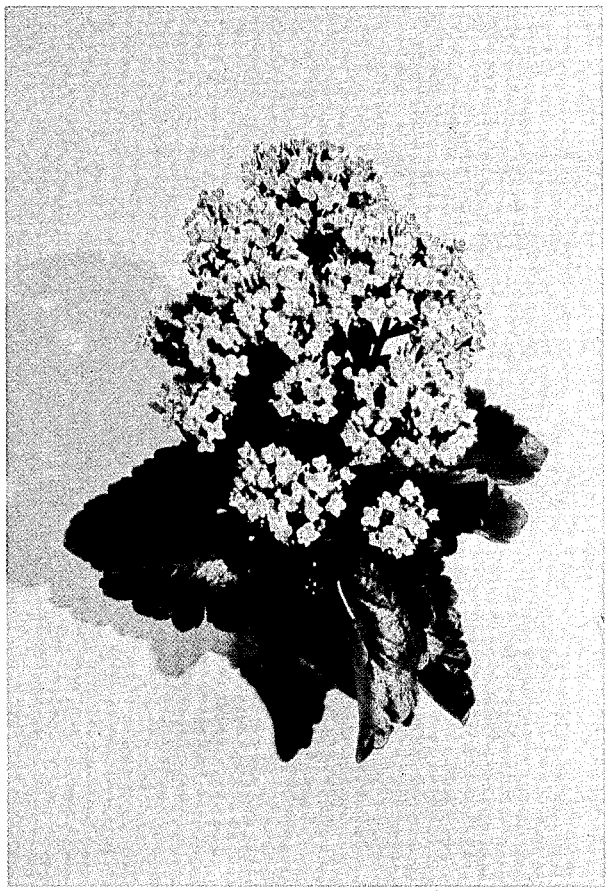

Grob

[11] Plant 4,102

[45] Sept. 13, 1977

[54] KALANCHOE PLANT

[75] Inventor: Adolf Grob, Saint Gall, Switzerland

[73] Assignee: Mikkelsens, Inc., Ashtabula, Ohio

[21] Appl. No.: 709,281

[22] Filed: July 28, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Donald D. Jeffery

[57] ABSTRACT

This invention relates to a mutation of the Feuerwerk Kalanchoe, differing therefrom by having a more distinct flower color, larger and more distinct foliage, and better overall growth qualities.

2 Drawing Figures

1

The present invention relates to a new and distinctive cultivar of Kalanchoe plant, botanically known as Kalanchoe and known by the cultivar name Feuerwerk II, discovered by me near Saint Gall, Switzerland as a mutation of the unpatented cultivar Grobs Feuerwerk. Asexual reproduction by stem cuttings of the new cultivar has shown that the unique features of this new Kalanchoe are stabilized and are reproduced true to type in successive propagations.

The following characteristics distinguish the new Kalanchoe from both its parent cultivar and other cultivated Kalanchoes of this type known and used in the floriculture industry:

1. In comparison to my cultivar Feuerball, disclosed in U.S. Plant Pat. No. 3,861, the foliage of Feuerwerk II is considerably larger and more distinct with highly crenated margins. Leaves have some tendency to cup upward with slight twisting.

2. In comparison to Feuerball, the flower peduncles of Feuerwerk II are thicker and stronger and have a more open placement of flowers.

3. Feuerwerk II has larger flowers than Feuerball. Flowering occurs 7 to 10 days earlier than either Feuerball or Feuerzauber, the latter being disclosed in my U.S. Plant Pat. No. 3,853.

4. When compared to Feuerball, the flower color of Feuerwerk II is an attractive shade of dark red but not as bright as the color of the flowers of Feuerball.

5. As contrasted to Feuerball, Feuerwerk II has better overall growth qualities, for example, being 20–25% taller in growth when compared to Feuerball under similar growing conditions.

6. The plant growth of Feuerwerk II more closely resembles Feuerzauber, but Feuerwerk II has a more pleasing placement of higher quality foliage and more distinct flower color.

7. Flower placement, flower size and quantity, and keeping quality of the flowers are all improved in Feuerwerk II when compared to Feuerzauber and Feuerball.

8. Flowering of Feuerwerk II can be manipulated for anytime of the year by applying modern forcing techniques. Feuerwerk II does not show adverse affects or heat delay during summer months.

9. The flowers of Feuerwerk II do not fade as drastically as Feuerzauber under high light and high temperature conditions.

10. The flowers of Feuerwerk II do not fade as drastically as Feuerzauber under high light and high temperature conditions.

2

The accompanying colored photograph illustrates the overall appearance of the new cultivar in perspective view, showing the colors as true as it is reasonably possible to obtain in a colored reproduction of this type.

The following is a detailed description of my new Kalanchoe cultivar based on plants produced under commercial practices in Switzerland in 10 cm. pots during the spring months March through May at 18° C night temperature. Color references are made to the Royal Horticultural Society Colour Chart except where general terms of ordinary dictionary significance are used.

Parentage: A selected mutation of Grobs Feuerwerk.

Propagation:

*Type cutting.*—Short stem cuttings approximately 2 cm. long.

*Time to root.*—14–18 days at 20°–22° C summer.

*Rooting habit.*—Quite rapid, with fibrous dendritic roots 4–5 cm. long on the above timing.

Plant description:

*Form.*—Upright, close internode compact growth, with very slight tendency to self branch until apical tip has been removed or flower induction has been initiated. Branches very well after manually pinching.

*Habit of growth.*—Is considered a medium grower, being approximately 25 cm. high (tall) in 10 cm. pot with total of 12 weeks growth during late winter and early spring months.

*Foliage description.*—Medium green, large foliage with double crenated edges that produce an attactive base for the red inflorescence. Size: Mature foliage up to 10 cm. wide by 12 cm. long, petiole short, 7–10 mm. long. Shape: Elliptical to ovate, apex obtuse, base obtuse. Texture: Glabrous, coriaceous. Margin: Doubly crenate. Color: Mature foliage, top side green between 137A and B, underside approximately 138A.

Flowering description:

*Flowering habits.*—Central inflorescence up to 10–12 cm. in diameter, laterals 6–8 cm. in diameter, compound paniculate cymes, central flowers opening first, total flowering up to 2 months.

*Natural flowering season.*—Begins mid to late January and continuing for 8–10 weeks. Flowering time under controlled daylength at 20° C in summer is 11–12 weeks; in winter is 14 weeks. Flowering can be forced at anytime of year by manipulation of environment.

*Flower bud description.*—Long, slender, bulbous at outer end before opening, up to 17 mm. long, 3 mm. in diameter prior to opening, calyx green.

*Flowers borne.*—Peduncles are strong and 7–8 mm. in diameter, extending upwards 10–12 cm. before the branching of the primary pedicels. Flowers are displayed at various levels of compound paniculate cyme, each cluster quite uniform.

*Quantity of flowers.*—Above average in number, but not all flowering at the same time, up to 50–60 per main inflorescence.

*Petals.*—Shape: Nearly round, slightly pointed, 6–7 mm. in diameter. Color: Top side when opening between 42A and 44A, fading to 42B; underside near 38A. Number of petals: Four, total flower size up to 16–18 mm. in diameter.

*Reproductive organs.*—Stamens: Eight in number. Anther shape: Flat, color brown; Filament color: Light green to yellow green; Pollen color: Bright yellow. Pistils: Stigma shape: Flat, color light yellow/green; Style color: light green; Ovaries: Four in number, size 8 mm. long, color green.

Disease resistance: No evidence to date of any susceptibility to mildew; quite resistant to botrytis stem rot during winter months.

It should be noted that environmental conditions such as temperature, light and especially soil moisture and nutrients greatly affect the size and color of foliage and flowers of Kalanchoes because of thier succulent type of growth.

I claim:

1. A new and distinct cultivar of Kalanchoe known by the cultivar name Feuerwerk II and particularly characterized as to uniqueness by the combined characteristics of relatively large foliage with highly crenated margins; relatively thick and strong peduncles which provide a more open placement of flowers; relatively large, dark red flowers; excellent growth qualities and vigor, with the growth being upright and compact; excellent flower placement, flower size and keeping qualities, and by its resistance to fading under high light and high temperature conditions.

* * * * *

UNITED STATES PATENT AND TRADEMARK OFFICE

CERTIFICATE OF CORRECTION

PATENT NO. : PP-4102

DATED : September 13, 1977

INVENTOR(S) : ADOLF GROB

It is certified that error appears in the above-identified patent and that said Letters Patent are hereby corrected as shown below:

In the heading on page 1, Section [22] the filing date should be July 27, 1976.

In Column 1, line 5, "Saint Gall" should be --Saint Gallen--.

Signed and Sealed this

*Eleventh* Day of *April 1978*

[SEAL]

*Attest:*

RUTH C. MASON
*Attesting Officer*

LUTRELLE F. PARKER
*Acting Commissioner of Patents and Trademarks*

UNITED STATES PATENT OFFICE

CERTIFICATE OF CORRECTION

Patent No. PP-4102 Dated September 13, 1977

Inventor(s) Adolf Grob

It is certified that error appears in the above-identified patent and that said Letters Patent are hereby corrected as shown below:

Column 1, lines 49-51, should be deleted.

Signed and Sealed this

*Twenty-seventh* Day of *June 1978*

[SEAL]

*Attest:*

RUTH C. MASON
*Attesting Officer*

DONALD W. BANNER
*Commissioner of Patents and Trademarks*